US005533515A

United States Patent [19]
Coller et al.

[11] Patent Number: 5,533,515
[45] Date of Patent: Jul. 9, 1996

[54] SOLID STATE SPHINCTER MYOMETERS

[75] Inventors: John A. Coller, Weston; Bruce Nappi, Newton; Alan J. Lane, Waltham, all of Mass.

[73] Assignees: Foster-Miller, Waltham; Lahey Clinic Medical Center, Burlington, both of Mass.

[21] Appl. No.: 289,083

[22] Filed: Aug. 11, 1994

[51] Int. Cl.$^6$ .................................................. A61B 5/00
[52] U.S. Cl. ........................................ 128/748; 128/780
[58] Field of Search .................................. 128/675, 748, 128/774, 778, 780; 73/379.02, 379.03

[56] References Cited

U.S. PATENT DOCUMENTS

| | | | |
|---|---|---|---|
| 4,561,450 | 12/1985 | Byrant | 128/780 |
| 4,566,465 | 1/1986 | Arhan et al. | 128/778 |
| 4,809,710 | 3/1989 | Williamson | 128/748 |
| 4,815,472 | 3/1989 | Wise et al. | 128/75 |
| 4,873,990 | 10/1989 | Holmes et al. | 128/748 |
| 4,887,610 | 12/1989 | Mittal | 128/733 |
| 4,949,729 | 8/1990 | Haski | 73/379.02 |
| 5,109,870 | 5/1992 | Silny et al. | 128/780 |
| 5,117,840 | 6/1992 | Brenman et al. | 128/788 |
| 5,181,522 | 1/1993 | McEwen | 128/774 |

*Primary Examiner*—Max Hindenburg
*Attorney, Agent, or Firm*—Lappin & Kusmer

[57] ABSTRACT

A system for providing real-time measurements of constriction pressure applied by the inner surface of a body lumen, such as a sphincter, includes a probe comprising an elongated core member having a matrix of pressure transducer regions distributed over the surface of the elongated core member. The preferred matrix of pressure transducer regions is addressed by a first inner array of substantially parallel electrically conductive strips substantially conformed circumferentially to at least a portion of the elongated core member, the first array being disposed in overlapping relationship with a second outer array of substantially parallel electrically conductive strips, and substantially conformed axially to at least the same portion of the elongated core member, so as to provide a matrix of intersection regions. Each pressure transducer region is disposed at a corresponding intersection region, and is in electrical contact with both a electrically conductive strip of the first array, and a electrically conductive strip of the second array. In the preferred embodiment the strips of the outer array are mechanically decoupled from one another by axially-directed slits to allow each individual strip to respond independently under hydrostatically applied pressures. A method of making the probe from commercially available materials is also disclosed.

30 Claims, 10 Drawing Sheets

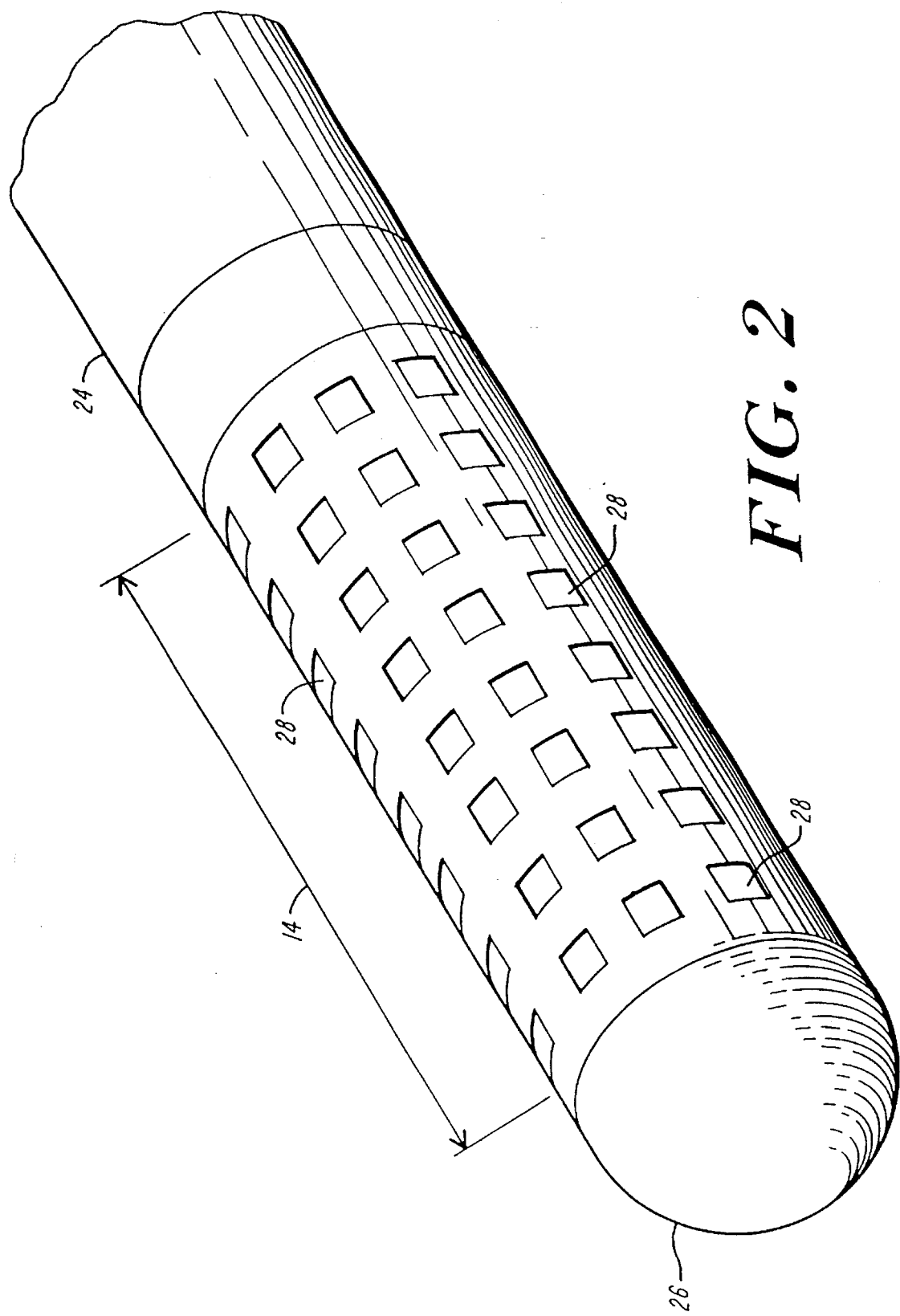

SOLID STATE SPHINCTER MYOMETERS

FIELD OF THE INVENTION

This invention relates generally to pressure measuring apparatus, and relates particularly to a probe for measuring constriction pressure exerted by the muscles of a sphincter.

BACKGROUND OF THE INVENTION

The human anorectal sphincter is a composite structure consisting of unique smooth and striate muscle, and having several anatomic configurations that are innervated from different sources. Both relaxation and contraction of the sphincter can occur simultaneously and at different loci within the sphincter. An adequate understanding of what is occurring at any single point, or at any single cross-sectional plane, is not always sufficient to understand the operation of the entire sphincter. Current recording mechanisms do not permit simultaneous assessment of discrete loci throughout the entire sphincter whether under voluntary control or in response to stimuli.

Numerous techniques have been used to assess various aspects of anorectal function. The techniques can generally be grouped into four categories: radiographic defecography, electromyography, rectal compliance, and anorectal sphincter manometry. Anorectal sphincter manometry, or perhaps more accurately "myography", typically uses measurements of fluid pressure to provide an objective assessment of various aspects of anorectal sphincter function. It provides a far more reliable indicator of the anal sphincter tone than can be achieved by digital examination. The relative contribution of the voluntary and involuntary components can be assessed, and the integrity of reflex inhibition to rectal distention can be evaluated. Moreover, the presence of an abnormal manometric pressure profile can provide insight regarding symptoms, etiology, and treatment.

In the most common sphincter manometry systems, such as a perfusion probe, fluid, typically in the form of an aqueous solution, is perfused at a constant rate through one or more small side ports in the probe. A transducer measures pressure to determine the resistance that the sphincter presents to perfused fluid. Another version of a perfusion probe is an infusion catheter. The catheter includes several holes near its end and radially arranged so that fluid can be pumped into the catheter and radially out through the holes. Measuring the back pressure on the perfused fluid provides a measure of the radially inward pressure exerted by the musculature of the sphincter on the catheter at the multiple locations of the holes. The holes are all circumferentially arranged around the catheter at a single axial position or in a close spiral pattern along the catheter. As a result, it is believed that the greatest number of holes used to date is eight. The close pattern of the holes results in only one position along the axis of the; sphincter being measured at any one time. Consequently, it is necessary to pull the catheter at a constant rate so that the perfusion holes travel along the entire length of the sphincter. Measurements are taken periodically as the catheter moves to provide a pressure profile of the entire sphincter. Good resolution is achieved when there are eight radially directed holes, circumferentially spaced around the catheter so that eight measurements can be taken simultaneously at each axial location.

Taking a sequence of pressure measurements at corresponding axial positions of the perfusion catheter over the inner surface of the sphincter has proven to be of assistance in assessment of a normal sphincter, and is a distinct improvement over prior less sophisticated methods. Typically, as the catheter moves, readings are taken every one-half millimeter, and consequently, assessing an entire sphincter can require some 2000 pressure readings and can take one hundred seconds. The readings are usually performed according to a protocol where, for example, the patient is required to relax and contract the sphincter, thereby squeezing the catheter. Data for each reading is stored in a separate file. Files are stored and various measurements are determined from the data, such as average pressure and maximum pressure.

A profile can also be drawn of the sphincter at each axial location that a reading is taken. Present systems use a chart recorder to record a sequence of readings. However, because the measurements for each reading are typically taken over one hundred seconds, noise and various artifacts are introduced. In addition, the amount of information that can be acquired is limited due to mechanical and physical limitations. For example, the number of perfusion channels that can be used is limited because as the number of channels increases, the amount of water required increases too, potentially resulting in patient discomfort and recording artifact. An alternative approach is to use multiple catheters, but this approach creates mechanical problems, since the device, is too large, and again, too much perfusion fluid is required. In addition, as the catheter is pulled, static and dynamic friction may result in incorrect readings. Also, during contraction maneuvers the patient can fatigue over the 100 seconds required to scan over an entire sphincter, resulting in some relaxation of the sphincter before the scan is complete. Finally, these devices tend to be very expensive.

Simultaneous multipoint recording has contributed substantially to the development of a more comprehensive picture of sphincter characteristics and action.

In addition to the perfusion probe, several other instruments have been developed for measuring a constriction pressure profile of a sphincter, including the anal, urethral, and esophageal sphincters. One type of probe employs a nueroballoon. Another approach uses pressure microtransducers on a catheter instead of perfusion holes. Nevertheless, the catheter must be pulled through the sphincter and readings sequentially taken to provide a complete assessment.

Further microtransducers, while being solid state, unlike the perfusion probes, are typically very expensive. In addition, a catheter based on known solid state microtransducers would be very large, and a catheter having a radial arrangement of known microtransducers at a single axial location on the catheter would still have to be pulled through a sphincter to acquire a complete pressure profile of the sphincter.

OBJECTS OF THE INVENTION

It is a general object of the present invention to provide an apparatus for measuring constrictive pressures exerted by sphincters that significantly overcomes the above-noted problems of the prior art.

A more specific object of the present invention is to provide a means for high-resolution mapping of constriction pressure applied by the musculature of a sphincter.

Another object of the invention is to provide a probe that can map constriction pressure over the inner surface of a sphincter without moving the probe.

And another object of the invention is to assess migrational and inter-relational aspects of motility waves within the sphincter complex.

Yet another object of the invention is to provide a probe that can map the pressure distribution applied by a sphincter without the inconvenience and complications of perfusion fluids.

Still another object of the invention is to provide a probe that can map the pressure distribution within a sphincter without producing the artifacts caused by motion-induced sphincter response.

And yet another object of the invention is to provide a probe that can provide simultaneous and real-time monitoring of the pressure over many points on the inner surface of a sphincter.

And still another object of the invention is to provide large amounts of diagnostic information regarding anorectal sphincter function, and enhanced ability to analyze the information.

And yet another object of the present invention is to provide a method of making the probe of a solid state sphincter myometer from commercially available materials.

Other objects of the present invention will in pan be suggested, and will in part appear hereinafter. The invention accordingly comprises the apparatus possessing the construction, combination of elements, and arrangement of parts, and the processes involving the several steps, and the relation and order of one or more of such steps with respect to the others, all of which are exemplified in the following detailed description, and are indicated in the claims.

SUMMARY OF THE INVENTION

The invention provides a sphincter myometer that includes a solid-state probe for the measurement and mapping of constriction pressure applied by the inner surface of a sphincter, or other portion of a body lumen, to the outer surface of the solid-state probe. The probe includes (a) an elongated cylindrical core member, (b) a first array of substantially parallel, electrically-conductive strips, electrically isolated from one another and substantially conforming to at least a portion of the elongated cylindrical core member, and (c) a second array of substantially parallel electrically-conductive strips, disposed in overlapping relationship with the strips of the first array so as to substantially conform to at least the same portion of the elongated core member and provide a matrix of intersection regions between the strips of the first array and the strips of the second array. The probe also includes means, disposed at each intersection region and cooperative with the corresponding electrically conductive strips of the first and second array, for measuring substantially radial forces applied to the intersection region.

A preferred embodiment of the present invention includes pressure-transducer material disposed between the strips of the first array and the strips of the second array at least at each intersection region. The pressure-transducer material preferably is characterized by a measurable resistance which varies as a function of the force applied normal to the material, throughout a range of forces (pressures) which includes the range of forces (pressures) of interest. The preferred material provides a resistance substantially inversely related to the amount of force applied normal to the material. Thus, the resistance decreases with corresponding increases in force applied normal to the material.

An addressable cylindrical matrix of pressure transducer regions is thus formed by the intersection of the two arrays of strips of electrically-conductive material and the pressure transducer material disposed there between. The electrically conductive strips can be sequentially addressed so that the resistance of the pressure transducer material disposed between each electrically conductive strip of the first plurality, and each electrically conductive strip of the second plurality can be measured.

Thus, each intersection of electrically conductive strips having pressure transducer material disposed therebetween results in an addressable pressure transducer region, and the two pluralities of overlapping electrically conductive strips provides an addressable matrix of pressure transducer regions. In a preferred embodiment, each plurality of electrically conductive strips includes sixteen electrically conductive strips, wherein the electrically conductive strips of the first plurality is wrapped circumferentially, and the second plurality of electrically conductive strips extend parallel to the longitudinal direction of the catheter and over the first plurality. Thus, a cylindrical cross-grid matrix pattern of electrically conductive strips forming a 32 by 16 matrix of (512) transducer regions is provided. Preferably, although not necessarily, the transducer regions are circumferentially equally spaced in longitudinal rows around the probe every 22.5°, and distributed in cylindrical rows along the axis of the probe at equally spaced intervals.

The matrix of addressable transducer regions is secured around the cylindrical surface of an elongated core member, which in a preferred embodiment is adapted to be inserted into an anal sphincter. The electrical resistance through the 512 intersecting points is preferably sequentially measured to provide a full scan. The pressure at each transducer region exerted by the sphincter is a function of the measured resistance measured at each region during the scan.

Finally, a method is provided for making the sphincter myometer probe from commercially available materials.

BRIEF DESCRIPTION OF THE DRAWINGS

The invention will be more fully understood from the following detailed description, in conjunction with the accompanying figures, wherein:

FIG. 2 is a schematic perspective view of the end portion of sensor probe of the sphincter myometer of FIG. 1, showing a cylindrical array of pressure transducers supported by an elongated cylindrical core member;

DETAILED DESCRIPTION OF THE DRAWINGS

Figure 1:
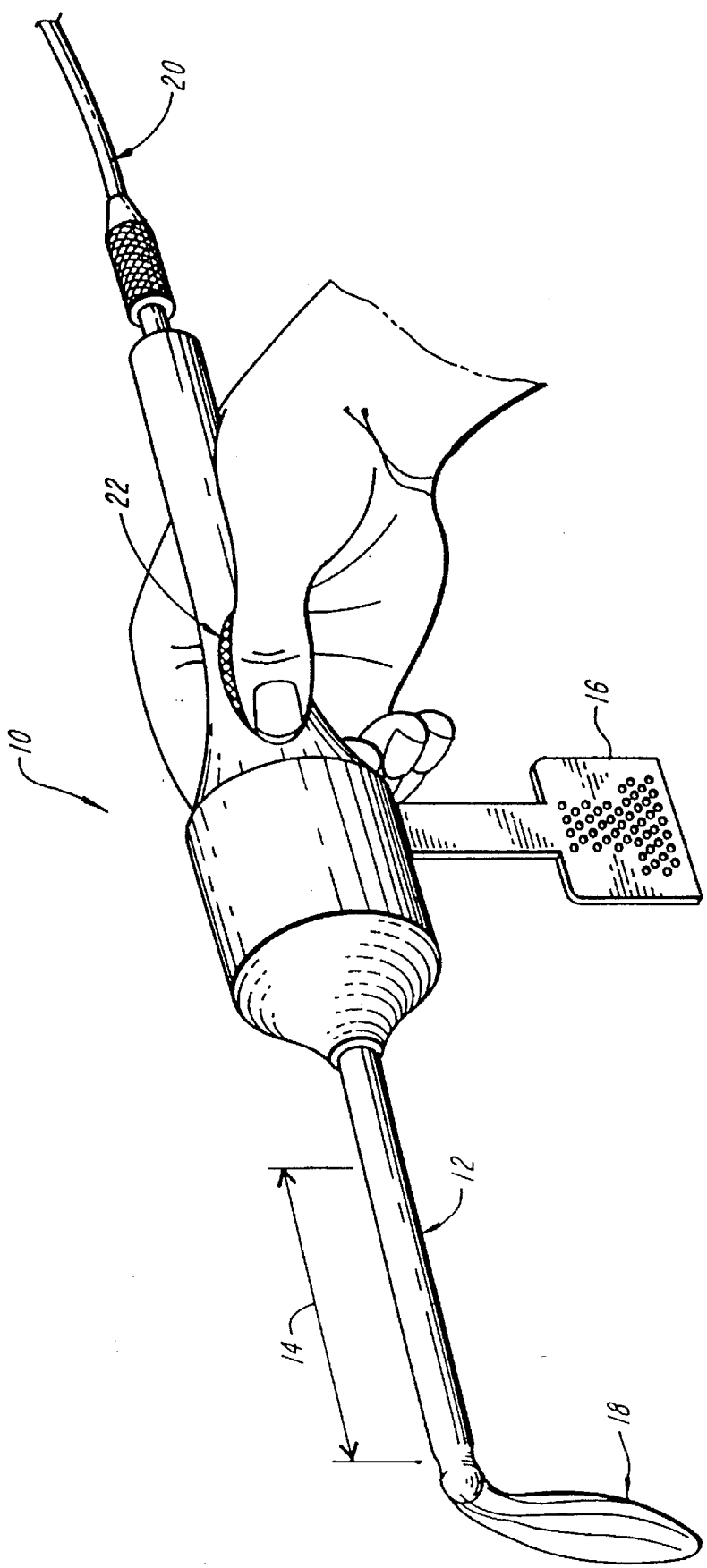
FIG. 1 is an artist's rendition of a hand-held embodiment of the sphincter myometer of the invention.
Figure 4:
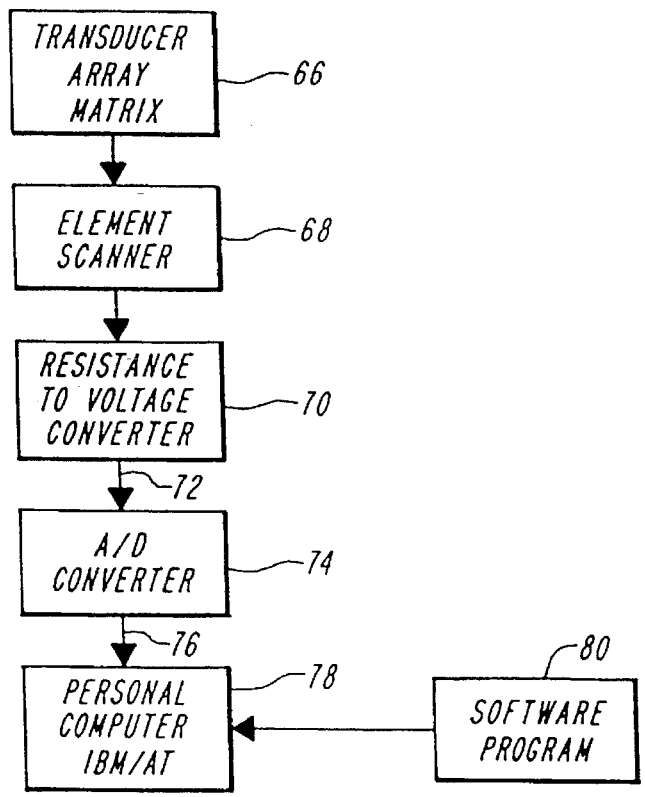
FIG. 4 is a block diagram of the transducer array of FIG. 2 connected to a data acquisition and analysis system.
Figure 5:
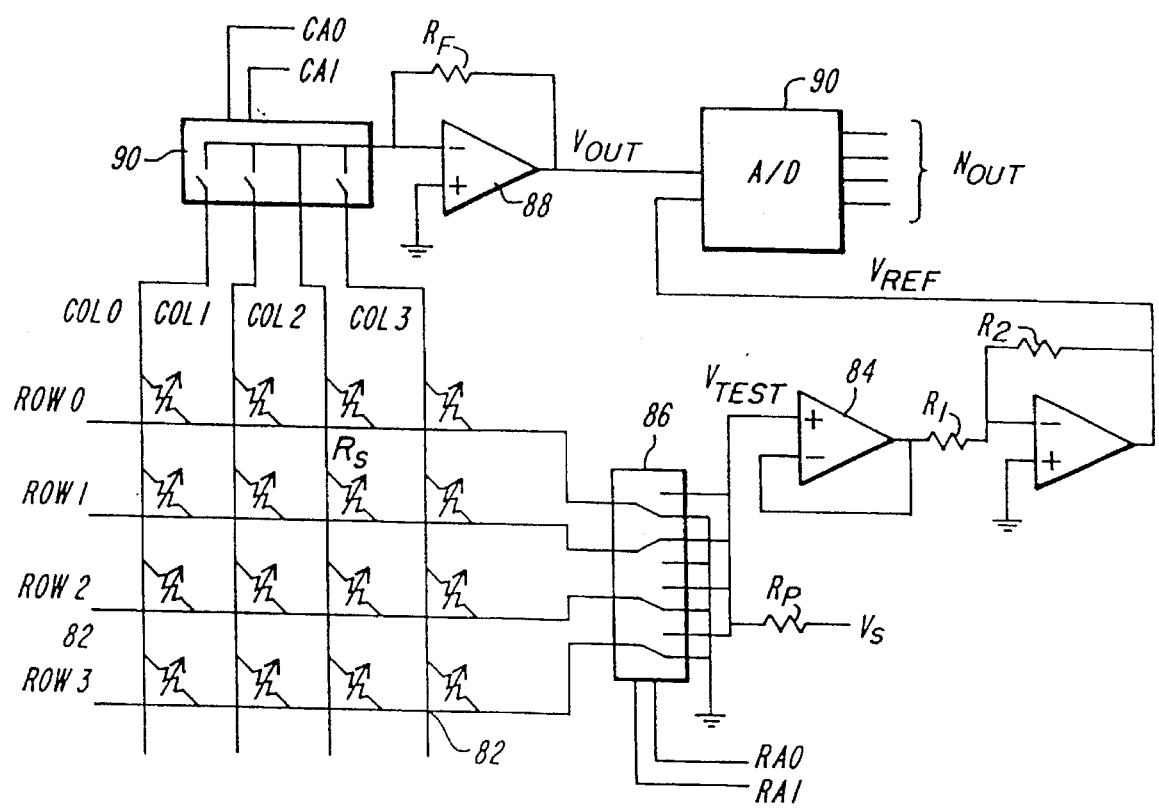
FIG. 5 is a more detailed partial block and partial schematic diagram of the data acquisition and analysis system of FIG. 4.
Figure 6:
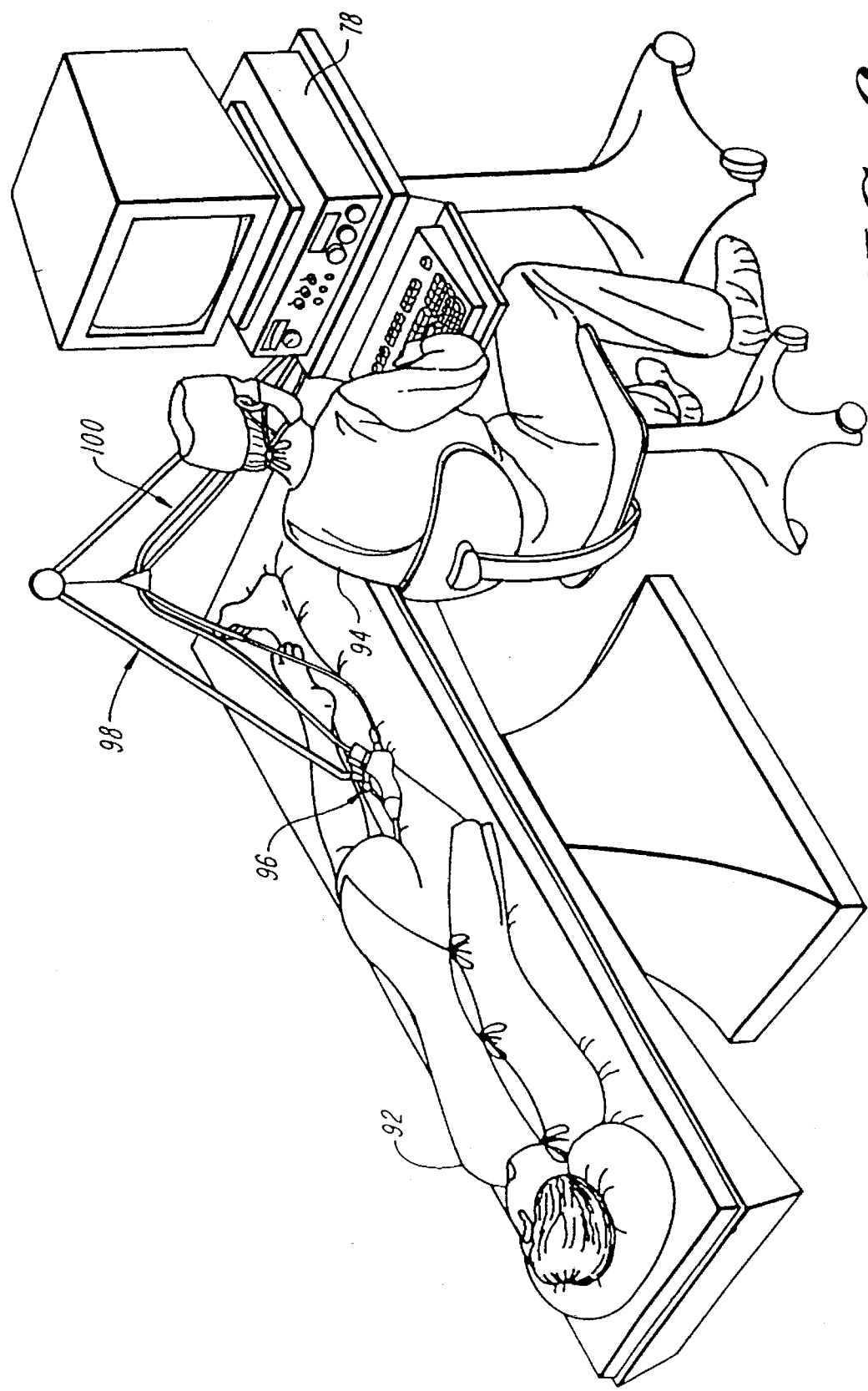
FIG. 6 is an artist's rendition of the sphincter myometer probe of the invention in use.

With reference to FIG. 1, a hand-held embodiment of the sphincter myometer probe 10 of the invention includes a cylindrical sensor probe 12 having a sensor region 14 for measuring pressure applied by a sphincter at a plurality of points on the surface of the sensor probe 12, and a sensor connector 16 for connecting the sensor probe 12 to means for acquiring and analyzing data (shown in FIGS. 4, 5 and 6). The sphincter myometer probe 10 also, although not necessarily, may include a balloon tip 18 for stimulating sphincter activity, a pneumatic line 20 for inflating the balloon tip 18, and a thumb grip 22 for firmly grasping and guiding the sphincter myometer probe 10.

Referring to FIG. 2, the preferred sensor probe 12 includes a rigid elongated cylindrical core member 24 that terminates at tip 26 for insertion into an anorectal sphincter. The elongated cylindrical core member can be rigid, to facilitate, for example, insertion into an anorectal sphincter, or it can be flexible, to facilitate access to an esophageal or urethral sphincter, for example.

A portion of the elongated cylindrical core member 24 supports a two-dimensional, cylindrical matrix of pressure transducer regions 28. Higher area-densities of pressure transducer regions can provide higher resolution pressure distribution maps. In an anorectal sphincter probe, a sensor matrix of sixty-two pressure transducer regions per square centimeter provides resolution sufficient to observe and analyze, for example, complex spatio-temporal patterns of sphincter muscle relaxation and contraction. (Each transducer region is approximately 0.0025 in$^2$ and using a conversion factor of $(0.3937)^2$ in$^2$/cm$^2$, each region is (0.0025/ 0.1549996)=0.016129 cm$^2$.) While the drawings for ease of illustration show a probe bearing a fewer number of transducer regions than that which is preferred, a typical anorectal probe has a surface area of at least eight square centimeters, and consequently would preferably include about 512 pressure transducer regions, although 256 and even a smaller number of regions seems to provide adequate resolution. Clearly, the precise number of regions chosen will depend upon and thus determine the resolution of the system.

In a preferred embodiment, the cylindrical matrix of pressure transducer regions 28 is formed by the corresponding intersections of two parallel arrays of strips of pressure transducer material, i.e., a circumferential array including parallel strips of pressure transducer material that each extend circumferentially around a portion of the elongated probe, and a longitudinal array consisting of parallel strips of pressure transducer material extending longitudinally along a portion of the elongated probe. At the intersection of each circumferential strip with each longitudinal strip, the circumferential strip makes electrical contact with the longitudinal strip so as to define the corresponding pressure transducer region. In addition, each strip of pressure transducer material is backed by a corresponding electrically conductive strip that is electrically connected to the strip of pressure transducer material along most of the length of the strip of pressure transducer material. Thus, it is possible to measure any force component applied radially to transducer region on the surface of the cylindrical core member 24 by measuring the resistance across the intersection of a longitudinal strip of pressure transducer material and a circumferential strip of pressure transducer material at the corresponding transducer region, i.e., by measuring the resistance across the corresponding electrically conductive strips at the transducer region.

Figure 2A:
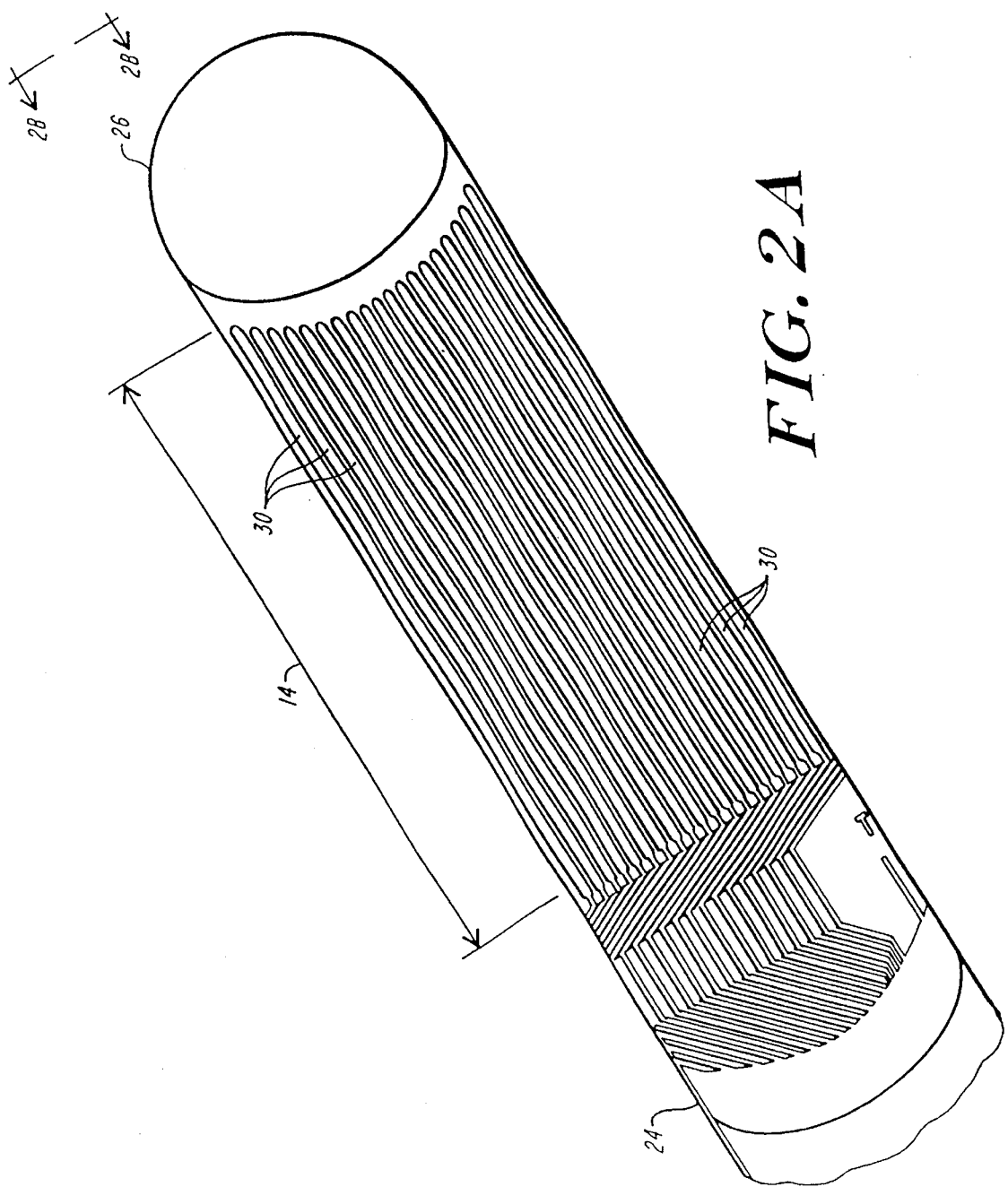
FIG. 2A is a detailed, partial, radial cross-sectional view of the sensor probe of the sphincter myometer of FIG. 1, absent its protective layer, showing an outer array of electrically conductive strips.
Figure 2B:
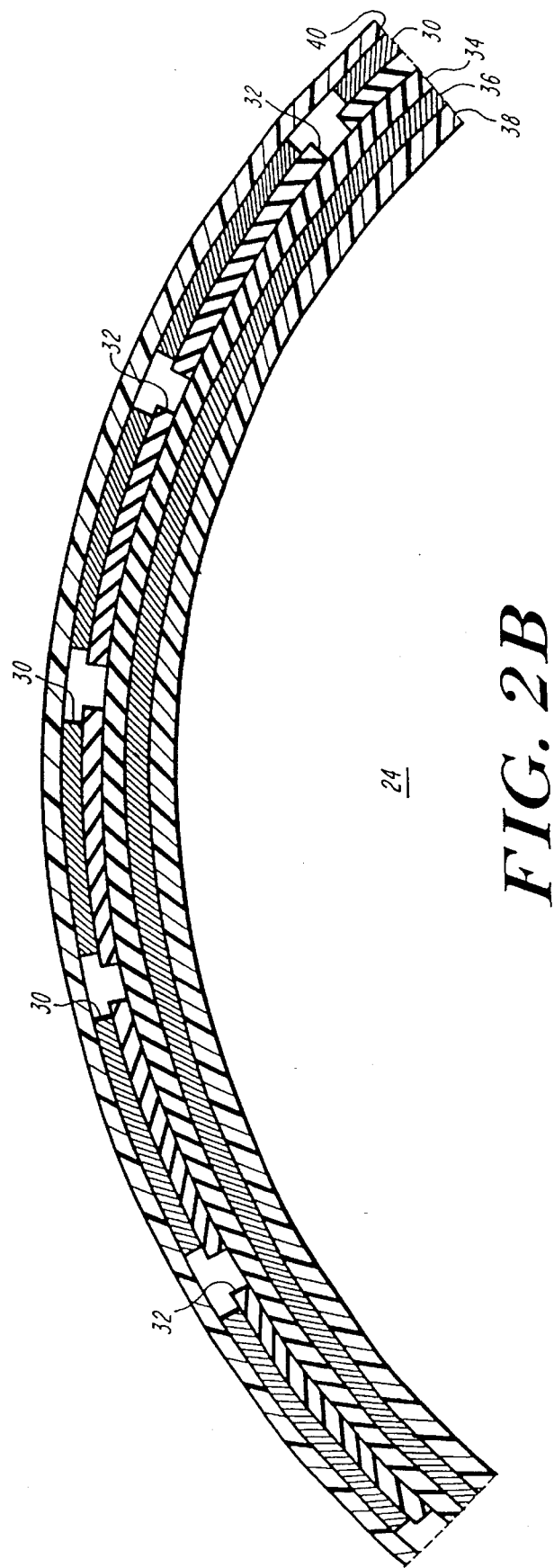
FIG. 2B is a detailed, partial, radial cross-sectional view of a portion of the sensor probe of FIG. 2A.

FIGS. 2A and 2B show a plurality of longitudinal electrically conductive strips 30. Underneath the electrically conductive strips 30, FIG. 2B, shows the corresponding longitudinal strips 32 of pressure transducer material, the intersecting circumferential strips 34 of pressure transducer material, and the corresponding circumferential electrically conductive strips 36. In addition, FIG. 2B shows outer and inner flexible support layers 38 and 40 that are made of a flexible material, such as mylar.

In a preferred embodiment, as described below the entire assembly of the layers comprising the strips 30, 32, 34 and 36 and layers 38 and 40 are commercially available as flat flex ribbon. As will be readily apparent, when flat flex, multiple layer ribbon is wrapped around a cylindrical surface the inner layers will require different dimensions around the circumference of the core member due to different radial spacings from the center of the core member. This results in operative problems of the individual transducer regions due to stress placed on the individual strip materials due to wrapping the materials around the cylindrical surface, i.e. the outer layers need to be tangentially stretched relative to the inner layers and/or the inner layers may need to be tangentially squeezed relative to the outer layers to accommodate the differences in the circumferential dimensions. Further, and even more significantly, a certain amount of "cross-talk" between adjacent transducer regions may occur, i.e. pressure applied to one region may incorrectly effect the reading of pressure at another region because all of the strips of each array are mechanically coupled together.

Figure 2C:
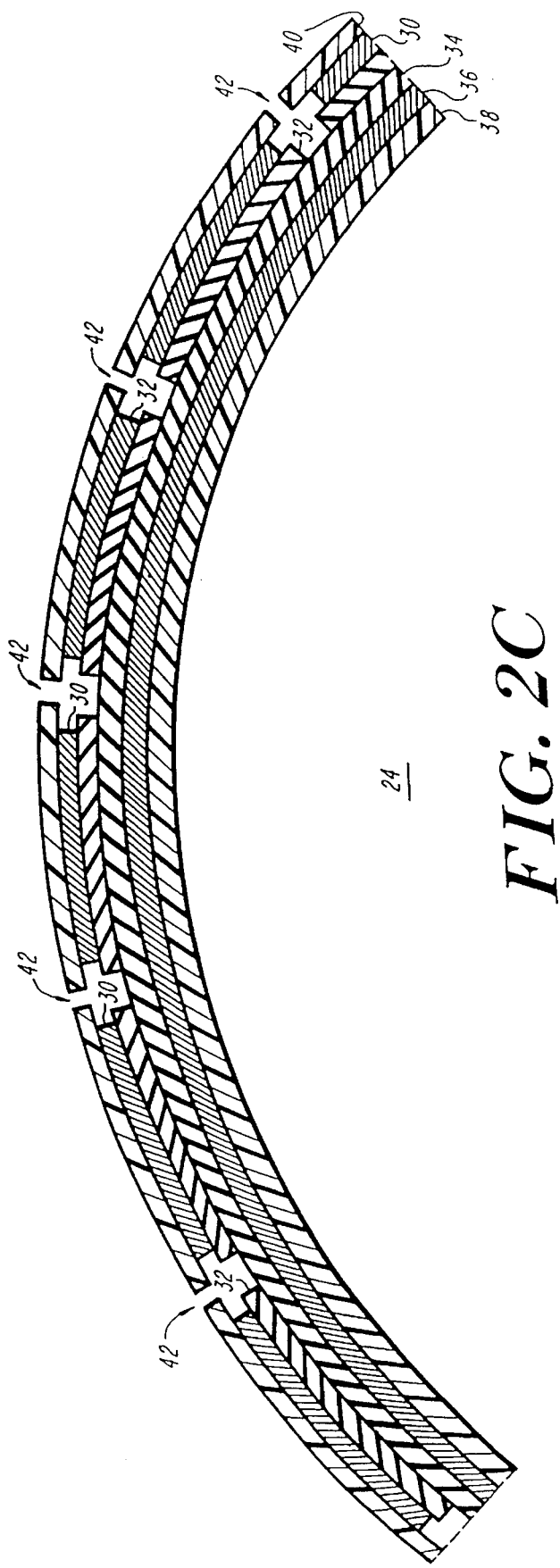
FIG. 2C is a detailed, partial, radial cross-sectional view of a portion of the sensor probe of FIG. 2A, further including slits in an outer support layer.

As shown in FIG. 2C, and accordance with the method of the present invention, in order to accommodate the increasing circumferential spacing with increasing radius, and in order to insure the longitudinal strips 30 and 32 respond independently under hydrostatic loading, the cylindrical matrix is disposed around the core member 24 so that the circumferential strips 34 and 36 are disposed inside the longitudinal strips 30 and 32 with minimal stress on the inside circumferential strips 34 and 36. The tension that would otherwise occur in the layers supporting the longitudinal strips 30 and 32, and the problem of cross-talk is minimized by mechanically decoupling the longitudinal strips from one another. More particularly, the outer support layer 40 includes a plurality of longitudinal slits 42 that are preferably created by removing a narrow longitudinal region of flexible material so as to substantially mechanically isolate or decouple each of the longitudinal electrically conductive strips 30 from the other longitudinal electrically conductive strips 30, and each of the longitudinal strips 32 of pressure transducer material from the other longitudinal strips 32 of pressure transducer material. This allows the strips 30 and 32 to be radially aligned and normal to forces applied in a radial direction to the cylindrical core member 24. To create the longitudinal slits 42, a laser can be used. For example, where the cylindrical core member 24 is 0.25" in diameter, 16 longitudinal electrically conductive strips, each 0.050" wide, are provided equiangularly (every 22.5°) around the circumference of the core member 24, slits 42 are, for example, each 0.001" wide. In this example, the circumferential strips are each 0.060" wide and spaced at 0.080" intervals along the axis of the cylindrical core member 24. Thus, once the slits 42 are formed, each longitudinal strip 32 of pressure transducer material, and the corresponding longitudinal electrically conductive strip 30, are independently supported by a separate supporting strip 40'.

Figure 2D:
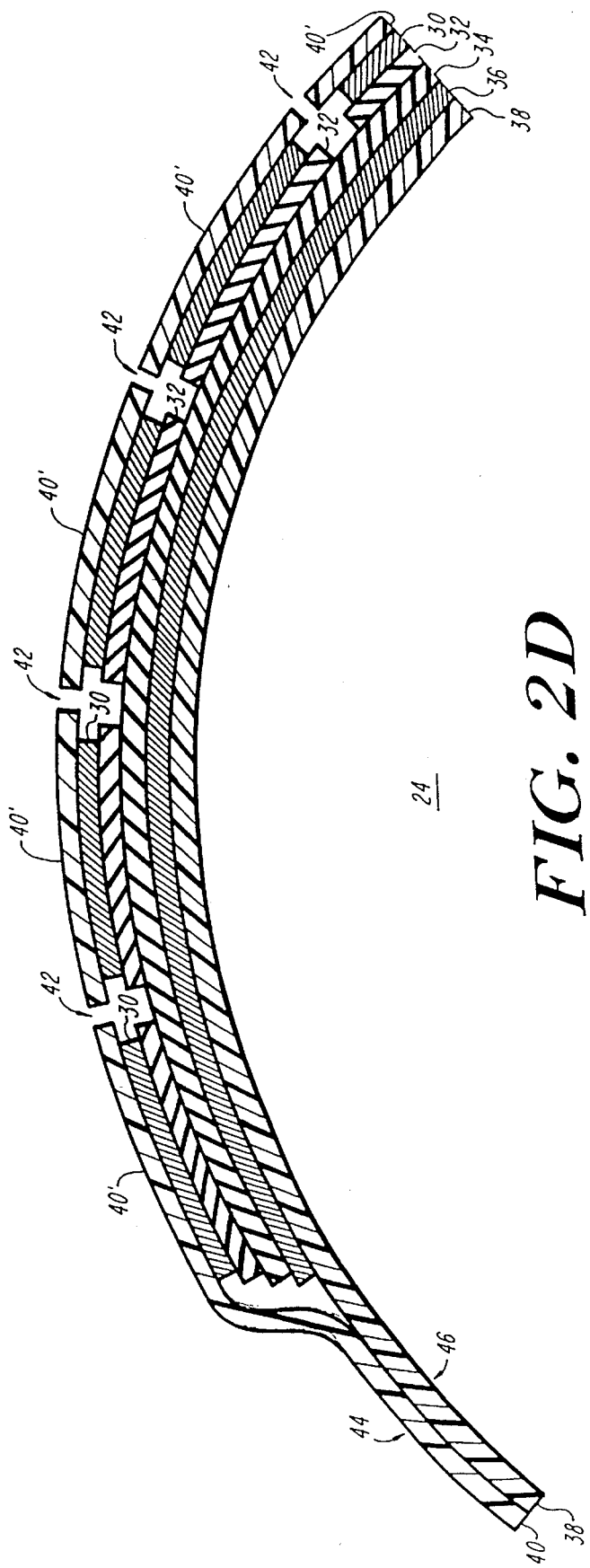
FIG. 2D is a detailed, partial, radial cross-sectional view of a portion of the sensor probe of FIG. 2A, further including a longitudinally extending region that bonds the outer support layer to an inner support layer.

FIG. 2D shows a partial cross-sectional view of an embodiment of the sensor probe of FIG. 2A, further including a longitudinally extending region (whose dimensions have been exaggerated for illustrative purposes) wherein a terminating portion 44 of the outer support layer 40 is bonded to a terminating portion 46 of the inner support layer 38. To provide a cylindrical matrix of pressure transducer regions distributed over the surface of the elongated cylindrical core member 24, the terminating portion 46 is bonded to the elongated core member 24 along a longitudinal line on the surface of the elongated core member 24. The layers comprising strips 30, 32, 34 and 36, and layers 38 and 40 are then wrapped around the elongated core member 24 so as to cover substantially the entire circumference of the elongated cylindrical core member 24. The process of wrapping increases the circumferential distance between the supporting strips 40', as well as the distance between the strips 30 and 32. This increase is easily accommodated by the slits 42 without creating tension in the layers supporting the strips. Mechanically isolating the longitudinal strips from one another results in substantially eliminating cross-talk between adjacent transducer regions so that the regions will work independently of one another under hydrostatic load.

Figure 2E:
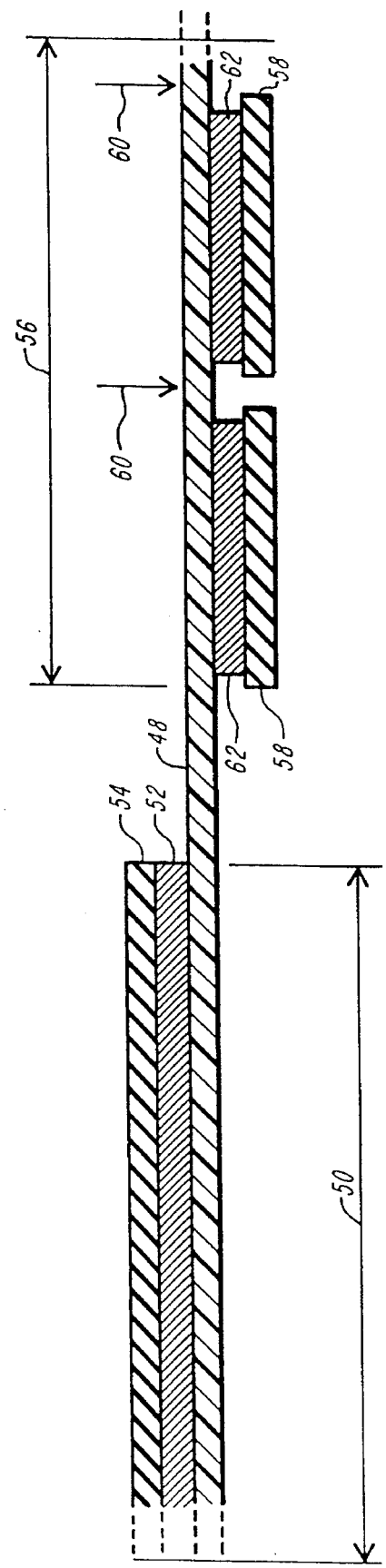
FIG. 2E is a detailed, cross-sectional view of a multi-layer structure adapted to be wrapped around an elongated cylindrical core member so as to provide a circumferential, cylindrical array of pressure transducers.

FIG. 2E shows another preferred embodiment wherein a support layer 48 serves as both an inner support layer and art outer support layer. To provide a cylindrical matrix of pressure transducer regions 28, the support layer 48 is circumferentially wrapped around elongated cylindrical core member 24 such that the circumferential portion 50 of the support layer 48 serves as an inner support layer, the circumferential portion 50 being; of a length sufficient to traverse substantially the entire circumference of the elongated cylindrical core member 24. The circumferential portion 50 of the support layer 48 supports a plurality of circumferential electrically conductive strips 52, each strip of which supports a circumferential strip 54 of pressure transducer material.

Next, a longitudinal portion 56 of the support layer 48 is wrapped around the elongated cylindrical core member, so as to serve as an outer support layer, the longitudinal portion 56 being of a length sufficient to traverse substantially the entire circumferential portion 50 of the support layer 48. Wrapping the longitudinal portion 56 brings a plurality of longitudinal strips 58 of pressure transducer material into intersecting electrical contact with the plurality of circumferential strips 54, thereby providing a cylindrical array of pressure transducer regions 28. Preferably, the spacing between the longitudinal strips can be adjusted during the fabrication of the FIG. 2E embodiment, or alternatively longitudinal slits, about as long as the longitudinal strips 58, are made at locations of the support layer 48 to promote mechanical isolation or decoupling of the longitudinal strips 58 of pressure transducer material, and the associated longitudinal electrically conductive strips 62.

After wrapping of either the embodiment of FIG. 2D or 2E, a protective layer in the form of a sheath, preferably made of an elastomeric material and shown covering the sensor region 12 in FIG. 1, is applied over the entire circumferential array of pressure transducer regions 28 so as to substantially conform to and enclose at least a portion of the elongated cylindrical core member 24. In a preferred embodiment, the protective layer substantially encloses all of the layers comprising strips 30, 32, 34 and 36, and layers 38 and 40 that together form the circumferential array of pressure transducer regions 28. The protective layer allows longitudinal strips of pressure transducer material, and the associated longitudinal electrically conductive strips to move and respond independently of each other, and nevertheless remain at substantially the same circumferential and radial positions, even when the supporting layer has been longitudinally slit. Thus, the protective layer ensures that pressure readings taken over a period of time are all accurately associated with a circumferential position.

The invention employs solid state pressure transducer technology. Traditionally, a force-to-electrical conversion has been performed primarily with strain gauges and piezoelectric devices. In a preferred embodiment of the invention, a pressure transducer material is used that is characterized by an electrical resistance that changes in response to force applied to the material. One example of such a pressure transducer material is called a "force sensing resistor", or "FSR", and is available in the form of flat flex ribbon (comprising a matrix of two parallel arrays of electrically conductive strips with the pressure transducer material disposed in between) from, for example, Interlink Electronics Corporation (Carpinteria, Calif.), or from Tekscan, Inc. (Boston, Mass.). FSRs are typically flat, polymer thick film devices which exhibit a decrease in electrical resistance with increasing applied force and can be modified as described above. The exact electromechanical characteristic of an FSR is a function of substrate type and thickness, conductor geometry, and electrically conductive polymer formulation. Lead attachment is typically accomplished by standard flex-circuit techniques.

Compared to sensing force using electrically conductive rubber, FSRs are lower in cost, have essentially zero travel, and do not change characteristics as readily after repeated cycling. This greater durability is in large part due to the extremely hard resistive material used in FSRs. FSRs have been made from 0.125 to 1.25 mm thick, and as small as 0.015 cm$^2$ in area. FSRs are superior for use in the solid state sphincter myometer of the invention as compared with the more common pressure measurement transducers, such as piezoelectric polymers and strain gauges. For example, piezoelectric transducers exhibit much higher speed and sensitivity to pressure changes than do FSRs, but they cannot sense static pressure. The higher speed and sensitivity of piezoelectric transducers causes them to pick up unwanted acoustic and vibrational signals. Strain gauges, while extremely accurate, are not sufficiently rugged, and are too costly.

Figure 3:
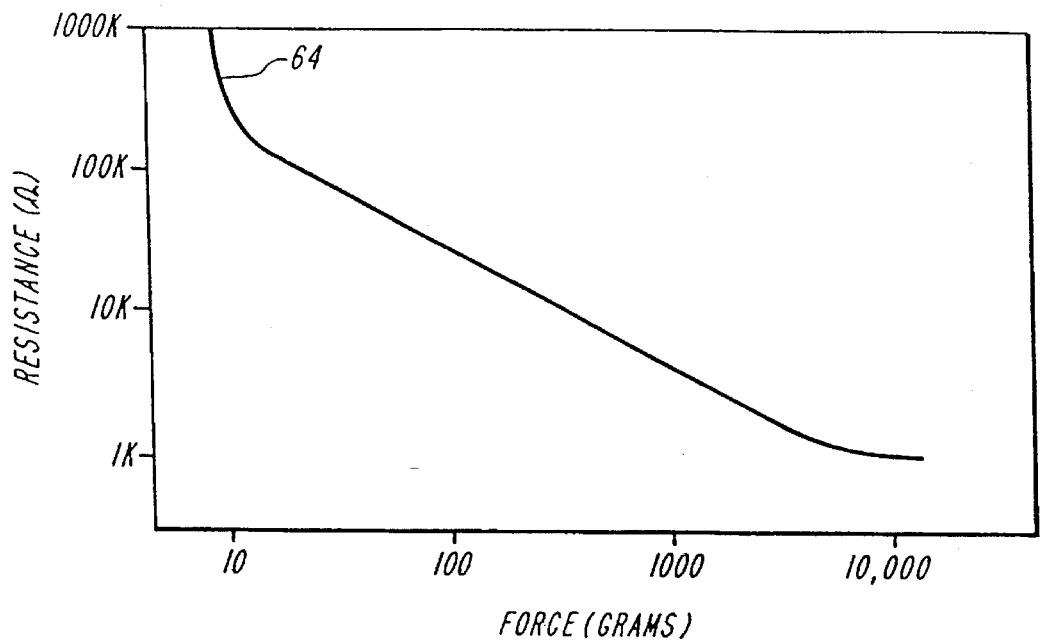
FIG. 3 is a graph showing the relationship between resistance and force applied in a direction normal to a pressure transducer region in accordance with the teachings of the present invention.

With reference to FIG. 3, a plot is shown of resistance as a function of force applied to a force sensing resistor having an area of 1 cm$^2$, and a thickness of about 0.005". Note that resistance is markedly high for low applied forces, i.e., applied forces of less than about 10 grams, as shown by the portion of the curve indicated by the reference numeral 64. Thus, when no force is applied to a force sensing resistor, the resistance is effectively infinite with effectively no current being permitted to flow through the force sensing resistor. As higher forces are applied, the resistance decreases. Thus, by measuring the electrical resistance of the force sensing resistor, the force applied to the force sensing resistor can be deduced from a knowledge of the way its resistance varies with applied force.

The transducer regions 28 of FIG. 2 provide a useful map of force applied to the cylindrical surface of the elongated core member 24 when they are arranged as a regular matrix of transducer regions 28 over the surface of the elongated cylindrical core member 24. FIG. 4 shows a block diagram of the elements of a system for acquiring, analyzing, and displaying the data obtained from a transducer region matrix 66, such as the matrix of transducer regions 28. Signals from each of the transducer regions 28 of the matrix 66 are acquired by an element scanner 68. In the preferred embodiment that uses FSR's, a resistance-to-voltage converter senses the resistance of each transducer region 28 and provides an analog voltage signal 72 in accordance with the resistance sensed. An analog-to-digital (A/D) converter 74 transforms the analog voltage signal 72 into a digital signal 76 representative of the resistance of a transducer region 28, and thus a function of the force applied radially to the region. A computer 78, such as an IBM PC/AT, receives the digital signal 76, and uses software 80 to perform data acquisition, first order data correction, data analysis and display.

Referring to FIG. 5, each pressure transducer region 28 is formed by the intersection of two strips of pressure transducer material. Each intersection, such as the intersections 82, is characterized by a resistance that depends on the force radially applied to the intersection of the strips of pressure transducer material. To measure the resistance across each intersection of two strips of pressure transducer material, the resistance across the corresponding electrically conductive strips is measured.

To perform the functions of the blocks 68 and 70 of FIG. 4, the resistance values at the intersections, i.e., the pressure transducer regions, are read out individually using the circuit, for example, shown in FIG. 5. In this circuit, to measure the value of the resistance $R_S$ at row 1, column 2, all rows except row 1 are set to ground. Row 1 is set to a reference voltage, $V_{test}$ at the non-inverting input of op-amp 84 via the CMOS SPDT analog switch 86. Column 2 is then also set to ground potential, but by way of the virtual ground potential of an operational amplifier 88. This allows the op-amp 88 to measure the current flowing out of column 2. Because column 2 and rows 0, 2, 3 are at ground potential, no current flows through their interconnecting resistors. Only the target resistor contributes to the current. The result is that each resistance value can be measured individually, even with only row-column wiring. In a preferred embodiment, a plurality of values are read out sequentially at a 1 KHz scan rate using the modules 86 and 90, and the scan control signals CA0, CA1 for addressing each particular column, and the scan control signals RA0, RA1 for addressing each particular row.

To perform the function of the A/D converter 74, in a preferred embodiment, a ratiometric analog-to-digital converter 90 provides a plurality of digital signals $N_{OUT}$ representative of the measured pressure distribution to be processed by the computer 78 and subsequently to be displayed by an operator.

Referring to FIG. 6, a patient 92 and an operator 94 are shown, wherein the operator 94 is monitoring the display of a computer 78 that is connected to an embodiment 96 of the sphincter myometer of the invention that is adapted to be supported by an extendable arm 98. The arm 98 also supports a pneumatic tube 100 that is connected to a source of pressurized gas (not shown) for inflating a balloon at the end of the probe that expands so as to apply pressure within the rectum, and thereby stimulate contractions and expansions of the sphincter musculature.

While the measurement of force is provided as a function of measured resistance between an electrically-conductive strip of the first array and an electrically-conductive strip of the second array at each transducer region 28, it is noted that other parameters can be used to measure force. For example, the electrically-conductive strip of the first array and the electrically-conductive strip of the second array at each transducer region can be capacitively coupled, and the force measured as a function of the change in capacitance at each region 28.

The solid state sphincter myometer of the invention can be used as a diagnostic tool, as well as a screening tool, and has several advantages over the prior art. The device is a solid state, non-perfuse instrument, thereby eliminating the need for fluid pressure measurements and the need to pull the catheter during the measurement. The probe can map the pressure distribution applied by a sphincter without the inconvenience and complications of perfusion fluids. It is at least as accurate as the prior art perfusion instruments and eliminates the problems of those prior art devices. The device is capable of performing multiple scans, e.g., three, per second so that the device can process data fairly instantaneously, providing real-time performance. Simultaneous and real-time monitoring of the pressure over many points on the inner surface of a sphincter can therefore be easily accomplished. The system is capable of providing high-resolution mapping of constriction pressure applied by the musculature of a sphincter. The probe can map constriction pressure over the inner surface of a sphincter without moving the probe. The system makes it easy to assess migrational and interrelational aspects of motility waves within a sphincter complex. The system can map the pressure distribution within a sphincter without producing the artifacts caused by motion-induced sphincter response. The system provides large amounts of diagnostic information regarding anorectal sphincter function, and enhanced ability to analyze the information.

Other modifications and implementations will occur to those skilled in the art without departing from the spirit and the scope of the invention as claimed. Accordingly, the above description is not intended to limit the invention except as indicated in the following claims.

What is claimed is:

1. A system for measuring constriction pressure within a body lumen, said system comprising:

an elongated cylindrical core member;

a first array of substantially parallel, electrically-conductive strips substantially conformed to at least a portion of said elongated cylindrical core member;

a second array of substantially parallel, electrically-conductive strips, disposed transverse to and in overlapping relationship with said first array of substantially parallel electrically conductive strips, and substantially conformed to at least said portion of said elongated core member, so as to provide with said first array a plurality of pressure transducer regions around the circumference and along the axis of said core member; and means, disposed between said first and second arrays at said pressure transducer regions, for defining a predetermined, measurable parameter at each of said regions between the corresponding electrical conductive strips of the first and second arrays such that the parameter varies as a function of a force applied to each of said regions so that constriction pressure within a body lumen can be measured.

2. The system of claim 1, wherein said means for defining a predetermined, measurable parameter at each pressure transducer region includes a layer of pressure-transducer material in electrical contact with the corresponding strips of said first and second arrays.

3. The system of claim 2, wherein said pressure-transducer material is characterized by an electrical resistance that changes in response to applied pressure.

4. The system of claim 1, wherein each electrically conductive strip of said first array is coated with a layer of pressure-transducer material.

5. The system of claim 4, wherein each electrically conductive strip of said second array is coated with a layer of pressure-transducer material.

6. The system of claim 1, further comprising:

a protective layer substantially conformed to at least a portion of said elongated core member, and substantially enclosing said first and second arrays of substantially parallel electrically conductive strips.

7. The system of claim 1, wherein the elongated core member is a flexible catheter.

8. The system of claim 1, wherein the elongated core member is adapted for insertion into an anal orifice.

9. The system of claim 1, wherein each pressure transducer region is a solid state device.

10. The system of claim 1, further including:

a flexible sheet having a first side and a second side, a portion of said first side supporting said first array of substantially parallel electrically conductive strips, and a portion of said second side supporting said second array of substantially parallel electrically conductive strips.

11. The system of claim 10, wherein a portion of said flexible sheet defines a plurality of slits parallel to and in between said electrically conductive strips, said slits serving to substantially mechanically decouple each electrically conductive strip from other substantially parallel electrically conductive strips.

12. The system of claim 10, wherein each electrically conductive strip of said first array is coated with a layer of pressure-transducer material.

13. The system of claim 12, wherein each electrically conductive strip of said second array is coated with a layer of pressure-transducer material.

14. The system of claim 10, wherein said flexible sheet is in wrapped relationship with said elongated member such that said first array of substantially parallel electrically conductive strips is in overlapping relationship with said second array of substantially parallel electrically conductive strips so as to provide a plurality of intersection regions, and wherein each pressure transducer region is disposed at an intersection region of said plurality of intersection regions, and is in electrical contact with both a electrically conductive strip of said first array, and a electrically conductive strip of said second array.

15. The system of claim 1, further including:

a first flexible sheet having a first side, a portion of said first side supporting said first array of substantially parallel electrically conductive strips;

a second flexible sheet having a second side in confronting relationship with said the first side of said first flexible sheet, a portion of said second side supporting said second array of substantially parallel electrically conductive strips.

16. The system of claim 15, wherein said first flexible sheet is bonded to said second flexible sheet along at least a substantially straight line segment.

17. The system of claim 16, wherein said first flexible sheet is bonded to said second flexible sheet along a substantially straight line segment extending longitudinally with respect to said elongated core member.

18. The system of claim 15, wherein one of said first flexible sheet and said second flexible sheet defines a plurality of slits parallel to and in between said electrically conductive strips of said one flexible sheet, said slits serving to substantially mechanically decouple each electrically conductive strip from other substantially parallel electrically conductive strips.

19. The system of claim 15, wherein each electrically conductive strip of said first array is coated with a layer of pressure-transducer material.

20. The system of claim 19, wherein each electrically conductive strip of said second array is coated with a layer of pressure-transducer material.

21. The system of claim 15, wherein said first and second flexible sheets are in wrapped relationship with said elongated member such that said first array of substantially parallel electrically conductive strips is in overlapping relationship with said second array of substantially parallel conductive strips so as to provide a plurality of intersection regions, and wherein each pressure transducer region is disposed at an intersection region of said plurality of intersection regions, and is in electrical contact with both a electrically conductive strip of said first array, and a electrically conductive strip of said second array.

22. The system of claim 1, wherein said plurality of pressure transducer regions are adapted to remain stationary with respect to said body lumen while measuring constriction pressure therein.

23. The system of claim 1, further including:

data acquisition and display means, connected to said array of pressure transducer regions, for real-time data acquisition and display of signals provided by said array of pressure transducer regions.

24. The system of claim 23, wherein said data acquisition and display means includes:

means for multiplexing so as to provide substantially simultaneous readings of said plurality of pressure transducer regions.

25. The system of claim 23, further including:

analysis means, connected to said data acquisition and display means, for providing analysis of complex spatio-temporal pressure patterns.

26. The system of claim 1, further including:

an inflatable balloon attached to an end of said elongated core member.

27. The system of claim 26, further including:

means for inflating said inflatable balloon.

28. The system of claim 27, wherein said means for inflating said inflatable balloon includes a source of forced air in fluid communication with said inflatable balloon.

29. The system of claim 1, wherein said electrically-conductive strips of said first array are oriented substantially circumferentially around said core member, said electrically-conductive strips of the second array are disposed over the electrically-conductive strips of the first array and oriented substantially parallel to the elongated direction of said core member and perpendicular to the electrically-conductive strips of the first array, wherein said electrically-conductive strips of the second array are mechanically decoupled from one another so that said system is capable of measuring hydrostatic pressure.

30. The system of claim 29, wherein each of said first and second arrays are supported by a plastic sheet, said plastic sheet supporting said second array including a plurality of longitudinally directed slits, one slit disposed between each adjacent pair of electrically-conductive strips of the second array so as to mechanically couple the strips of said second array.

* * * * *